US009149433B2

(12) United States Patent
Lisa et al.

(10) Patent No.: US 9,149,433 B2
(45) Date of Patent: Oct. 6, 2015

(54) METHOD FOR FORMATION OF MICRO-PRILLED POLYMERS

(75) Inventors: Rudolph Ernest Lisa, Grosse Ile, MI (US); Anisul Quadir, Hackettstown, NJ (US); Rebecca Ham Scheper, Mount Arlington, NJ (US); Peter Grzesowski, Boonton, NJ (US)

(73) Assignee: BASF CORPORATION, Florham Park, NJ (US)

( * ) Notice: Subject to any disclaimer, the term of this patent is extended or adjusted under 35 U.S.C. 154(b) by 2238 days.

(21) Appl. No.: 10/999,580

(22) Filed: Nov. 30, 2004

(65) Prior Publication Data

US 2006/0115535 A1    Jun. 1, 2006

(51) Int. Cl.
*A61K 9/14* (2006.01)
*A61K 47/34* (2006.01)
*A61K 9/20* (2006.01)

(52) U.S. Cl.
CPC .............. *A61K 9/146* (2013.01); *A61K 9/2031* (2013.01); *A61K 47/34* (2013.01)

(58) Field of Classification Search
None
See application file for complete search history.

(56) References Cited

U.S. PATENT DOCUMENTS

| 3,250,830 A | * | 5/1966 | Lyon et al. ...................... 264/9 |
| 4,610,760 A | * | 9/1986 | Kirkpatrick et al. .......... 159/4.01 |
| 5,417,985 A | * | 5/1995 | Coutel et al. ................... 424/489 |
| 5,810,252 A | * | 9/1998 | Pennamen et al. ................. 239/8 |
| 6,013,280 A | * | 1/2000 | Frisbee et al. ................. 424/464 |
| 6,051,256 A | * | 4/2000 | Platz et al. ..................... 424/489 |
| 2003/0054045 A1 | * | 3/2003 | Liversidge et al. ........... 424/497 |
| 2003/0165681 A1 | * | 9/2003 | Hamer et al. ............. 428/402.22 |
| 2003/0215496 A1 | * | 11/2003 | Patel et al. ..................... 424/452 |
| 2004/0197406 A1 | * | 10/2004 | Prater et al. ................... 424/470 |
| 2005/0181060 A1 | * | 8/2005 | Friesen et al. ................ 424/489 |

FOREIGN PATENT DOCUMENTS

WO    WO2005053655    *    6/2005    .............. A61K 9/16

OTHER PUBLICATIONS

Burdock, G. Encyclopedia of Food and Color Additives, CRC Press, Inc., 1997, p. 2235.*
Kjaergaard, O., "Prilling-Multiple Core Encapsulation." GEA Process Engineering Inc., Aug. 2000, pp. 1-10, Accessed Aug. 10, 2009.*

* cited by examiner

*Primary Examiner* — Rachael E Bredefeld
(74) *Attorney, Agent, or Firm* — Howard & Howard Attorneys PLLC

(57) ABSTRACT

A method for formation of micro-prilled poloxamer particles is disclosed. The particles find special use in pharmaceutical formulations. The process involves use of atomizing nozzles at higher than normal pressure atomizing gas, high atomizing gas temperature, use of high feed temperatures to reduce the viscosity of the poloxamer and optionally sieving after prill formation in prilling towers. The poloxamer particles are spherical and preferably have an average nominal diameter of less than or equal to 106 microns. The process is very cost effective and rapid.

21 Claims, 7 Drawing Sheets

METHOD FOR FORMATION OF MICRO-PRILLED POLYMERS

RELATED APPLICATIONS

NONE.

STATEMENT REGARDING FEDERALLY SPONSORED RESEARCH

NONE

TECHNICAL FIELD

This invention relates generally to formation of micro-prilled polymers and, more particularly, to a method for formation of micro-prilled poloxamer particles useful in pharmaceutical formulations.

BACKGROUND OF THE INVENTION

Many current pharmaceuticals are very efficacious and potent, thus very small doses are needed to provide the desired benefit. This causes problems in formulation of the pharmaceutical into a consumer usable form. The difficulty is to devise a method to ensure that a consistent dose of the pharmaceutical is present in each tablet or other drug delivery form. A typical method for accomplishing this is to formulate tablets with a variety of additive agents to increase the size of a tablet to a usable size for consumers while optimizing the manufacturing process and the tablet end use properties. Classes of additives include fillers, binders, disintegrating agents, dissolving or solubilizing agents, lubricants, glidants, colorants, flavors, sweetening agents, and wetting agents. One difficulty associated with mixing a variety of powders into a single tablet is that if the particle sizes are different it can be difficult to achieve homogeneity of distribution of the various components in the final powder and therefore in the final tablet. This variation in the particle size of ingredients often results in the necessity of increasing the overage of the active drug ingredient in order to ensure a minimum potency in each and every tablet, resulting in additional amount and cost for the drug ingredient. Maintaining a small particle size reduces this variation.

Typical solubilizers include low melting polymers such as the poloxamer class of polymers. These polymers are block co-polymers of ethylene oxide and propylene oxide and have the advantage of being relatively low melting polymers with typical melting temperatures of from about 45 to 60° C. Thus, they are solid at room temperature, but melt readily at higher temperatures.

One way to ensure homogeneity of distribution of the various components in the final powder is to find a way to make all the powders have about the same particle size. Typically, the desired particle size is less than 200 microns and often less than 50 microns. The problem for the use of poloxamers is that their low melting temperature makes most milling practices impractical because the poloxamer either melts or is charred during the milling process. One solution has been the use of micro-milled poloxamer that is manufactured under cryogenic conditions, such as cooling the poloxamer to less than −70° C. then rapid milling. Preferably the milling is carried out at a temperature of less than −100° C. There are numerous problems associated with this solution the first being the cost to produce a micro-milled poloxamer. It requires the use of a cooling agent such as liquid nitrogen which is expensive. There is also a high labor component in part due to relatively low rates of production. The material must be warmed to avoid aggregation. The process is slow in part because it requires many steps. Finally, good manufacturing practices in the formation of pharmaceuticals require scrupulous attention to the detection and elimination of any potential contaminants. This is hard to do and costly with the cryogenic micro-milling process making it less desirable.

It would be desirable to develop a rapid, cost-effective process for formation of poloxamer particles that would enable them to be readily used in pharmaceutical formulations. Preferably the process will produce a high yield of the desired particles with minimal possibility of contamination from foreign material.

SUMMARY OF THE INVENTION

In one embodiment, this invention provides a plurality of micro-prilled poloxamer particles comprising: one or more copolymers of ethylene oxide and propylene oxide each having a general formula of $HO(C_2H_4O)_a(C_3H_6O)_b(C_2H_4O)_aH$, wherein a value of a is from about 60 to about 150 and a value of b is from about 25 to about 60 and the particles being spherical, solid at 25° C., and the plurality of particles having an average nominal diameter of less and or equal to 106 microns.

In another embodiment the present invention is a method for formation of a plurality of micro-prilled poloxamer particles comprising the steps of: providing at least one copolymer of ethylene oxide and propylene oxide having a general formula of $HO(C_2H_4O)_a(C_3H_6O)_b(C_2H_4O)_aH$, wherein a value of a is from about 60 to about 150 and a value of b is from about 25 to about 60; heating the at least one copolymer to a temperature sufficient to reduce its viscosity to less than or equal to 1300; atomizing the heated at least one copolymer by passing it through an atomizing nozzle and into one of a co-current or a counter-current prilling tower thereby forming a plurality of particles of the at least one copolymer, the plurality of particles having an average nominal diameter of less than or equal to 106 microns; and, optionally, sieving the plurality of particles formed and retaining the particles passing through a mesh screen having openings of about 106 microns.

These and other features and advantages of this invention will become more apparent to those skilled in the art from the detailed description of a preferred embodiment. The drawings that accompany the detailed description are described below.

DETAILED DESCRIPTION OF A PREFERRED EMBODIMENT

As discussed above the present invention is directed to a method for formation of micro-prilled poloxamers that find special use in the pharmaceutical industry as dispersants or solubilizers as well as fillers that effect time release properties. The poloxamers are a class of block co-polymers of ethylene oxide and propylene oxide having the general formula: $HO(C_2H_4O)_a(C_3H_6O)_b(C_2H_4O)_aH$, wherein a has a value of from about 60 to about 150 and b has a value of from about 25 to about 60. These are solids at a temperature of 25° C. and have low melting temperatures in the range of 45 to 60° C. Preferably the poloxamers have number average molecular weights of from about 6,000 to 18,000 Daltons. Specific examples are available from BASF corporation and include the following: Pluronic® F68NF also known as Poloxamer 188 with a having a value of about 80 and with b having a value of about 27; Pluronic® F87NF also known as Poloxamer 237 with a having a value of about 64 and with b having a value of about 37; Pluronic® F108NF also known as Poloxamer 141 with a having a value of about 141 and with b having a value of about 44; Pluronic® F127NF also known as Poloxamer 407 with a having a value of about 101 and with b having a value of about 56. These Pluronic® compounds are also designated as BASF Lutrol F grades. The present process also permits the use of mixtures of the poloxamers.

Figure 1A:
FIG. 1A is scanning photomicrograph of a poloxamer that has been micro-milled according to a prior art process at a magnification of 100×.
Figure 1B:
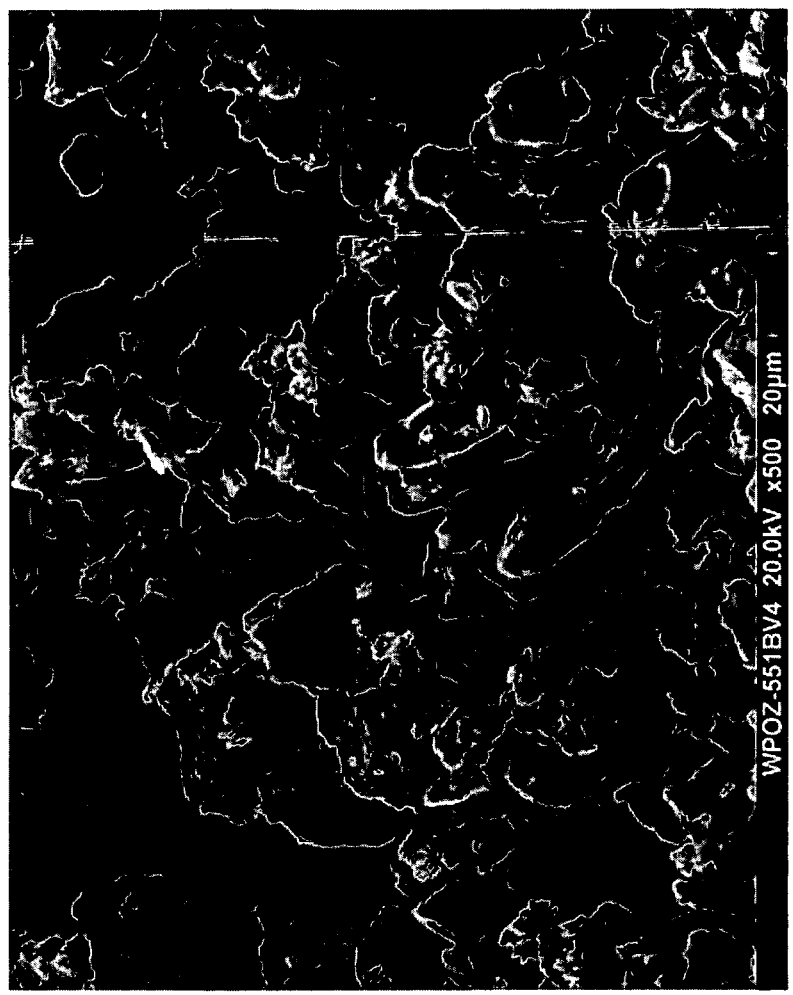
FIG. 1B is scanning photomicrograph of a poloxamer that has been micro-milled according to a prior art process at a magnification of 500×.

As discussed in the past poloxamers have been micronized using a cryogenic milling process, which is the subject of U.S. patent application Ser. No. 60/540,338, filed on Feb. 2, 2004. In brief, the process requires the use of a mill that can be chilled and that preferably has no moving parts that come into contact with the solid poloxamer as it is being milled. Such a mill is the Vortex Mill available from Super Fine Ltd. and described in U.S. Pat. No. 5,855,326. Preferably the mill is chilled with liquid nitrogen or chilled air to a temperature of below about −85° C. and more preferably, below about −100° C. The milling process uses pressurized inert gas at a pressure of from about 90 to 95 psig. The solid poloxamer is fed into the mill and milled. After milling the product is warmed to room temperature for 12 to 72 hours and then preferably sieved to obtain the desired particle size. FIGS. 1A and 1B are scanning photomicrographs of micro-milled Poloxamer 188 from BASF Corporation at two magnifications. FIG. 1A is a 100× magnification and FIG. 1B is a 500× magnification. It can be seen that the process produced may irregularly shaped particles. Many of the particles are plate-shaped or other irregular shapes. There is not a great deal of uniformity in the sizes or shapes of the particles.

As discussed above the micro-milling process is not entirely satisfactory for producing poloxamer particles for use in pharmaceutical processes. The present invention is directed to an alternative process for creating micronized poloxamer particles for use in pharmaceuticals.

The present invention is directed to an atomization process in combination with a sieving step to create micro-prilled poloxamer particles. In a typical prilling process a liquid polymer is directed through an atomizing nozzle into the top of a prilling tower. Such prilling towers are know in the art and will not be described in detail. In the prilling tower a chilled cooling gas is passed either co-currently or counter-currently past the falling droplets of the polymer and freezes them into solid particles. Preferably the chilled cooling gas is at a temperature of about −1° C. The nozzles used are generally two fluid nozzles or three fluid nozzles. The typical pressures of the atomizing gases are generally kept at between 50 to 70 psig. In general, prilling towers have been used to form large size prills of 400 to 1200 microns in diameter of various polymers. Typically the polymers are fed to the nozzles at temperatures of from 93 to 99° C. These conditions are unsuitable for producing micro-prilled poloxamer particles. Such particle sizes are far too large to be useful in a pharmaceutical formulation.

Figure 2A:
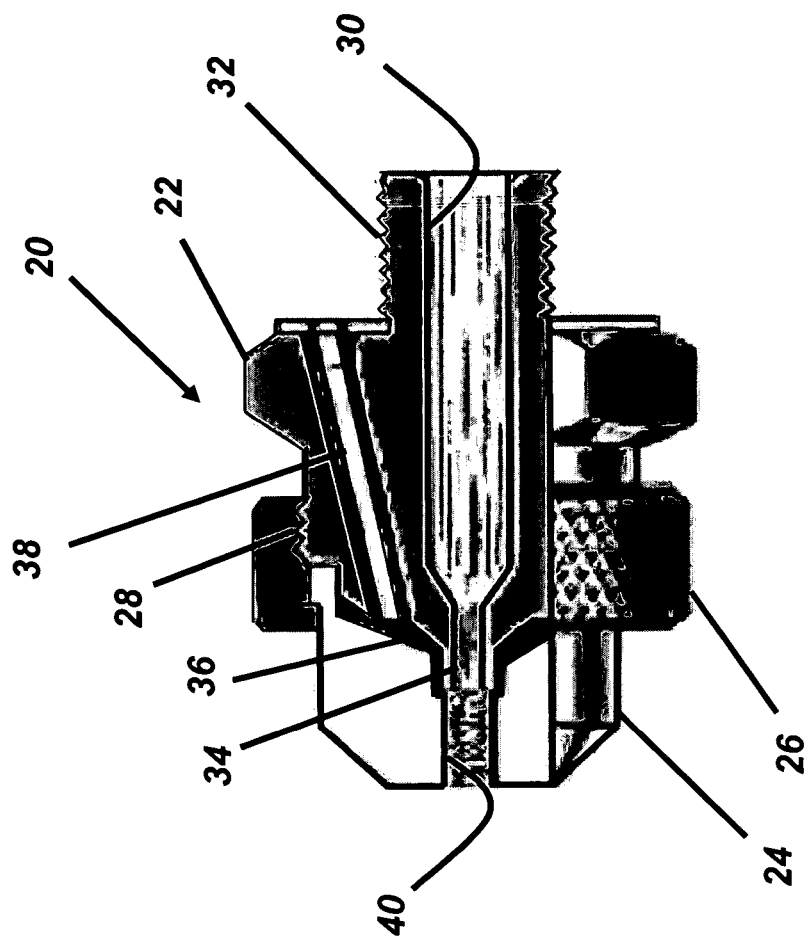
FIG. 2A is cross-sectional view of an internal mixing two fluid nozzle for use in the method of the present invention.
Figure 2B:
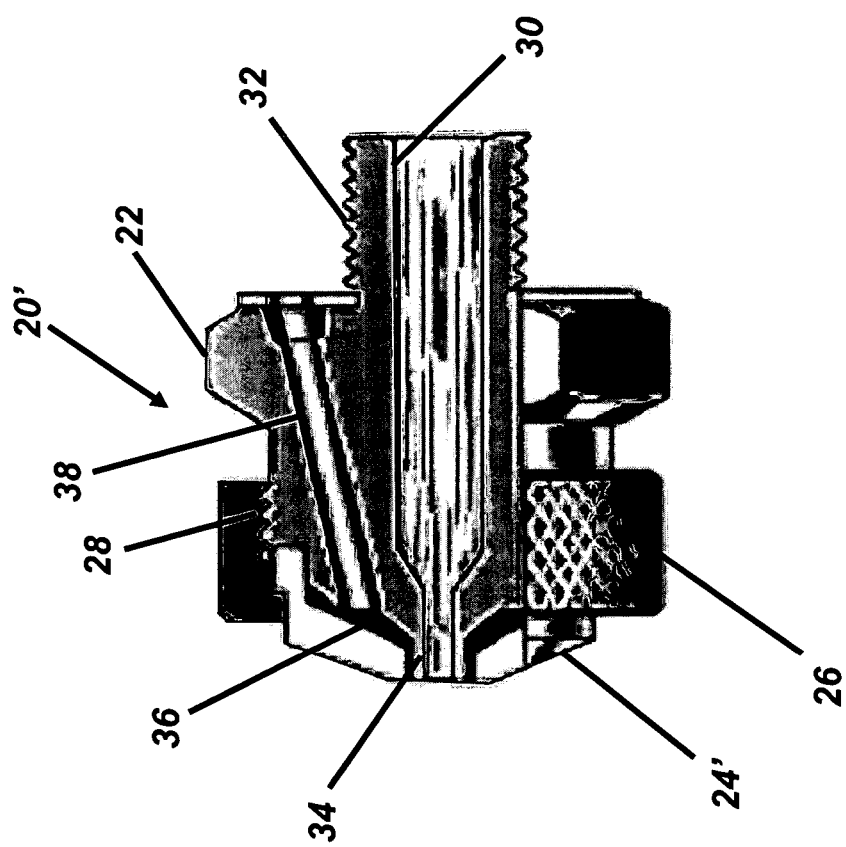
FIG. 2B is cross-sectional view of an external mixing two fluid nozzle for use in the method of the present invention.

A cross-sectional view of a typical internal mix two fluid nozzle is shown generally at 20 in FIG. 2A. The nozzle 20 includes a nozzle body 22 and a cap 24. A threaded ring 26 engages threads 28 on nozzle body 22 to secure the cap 24 to the nozzle body 22. Nozzle body 22 includes a central passage 30 having a central orifice 34. Nozzle body 24 further includes an outer passage 38 that connects to an outer orifice 36. The outer orifice 36 is concentric with the central orifice 34. The cap 24 also includes a mixing chamber 40. In use a poloxamer solution is pumped into the central passage 30 and exits the central orifice 34. An atomizing gas is fed into the outer passage 38 and exits the outer orifice 36. In the mixing chamber 40 the gas from the outer orifice 36 shears the poloxamer solution and forms droplets, which exit with the gas from the nozzle 20. Because the mixing of the gas and the liquid occurs in the mixing chamber 40 this is known as an internal mixing nozzle 20. A second style of two fluid nozzle is shown generally at 20' in FIG. 2B. This style is known as an external mixing nozzle 20' and either nozzle 20 or 20' can be used in the present invention. The external mix nozzle 20' is generally preferred because it keeps the nozzle 20' hotter and reduces plugging of the nozzle 20' especially when the prilling is temporally stopped. The external mixing nozzle 20' includes a nozzle body 22 and a short cap 24'. A threaded ring 26 engages threads 28 on nozzle body 22 to secure the cap 24' to the nozzle body 22. Nozzle body 22 includes a central passage 30 having a central orifice 34. Nozzle body 24 further includes an outer passage 38 that connects to an outer orifice 36. The outer orifice 36 is concentric with the central orifice 34. The cap 24' unlike the cap 24' above does not include a mixing chamber 40. In use a poloxamer solution is pumped into the central passage 30 and exits the central orifice 34. An atomizing gas is fed into the outer passage 38 and exits the outer orifice 36. The mixing of the gas and the liquid occurs outside the nozzle 20'. A plurality of nozzles 20 or 20' are mounted in the top of a standard prilling tower and feed atomized droplets into the co-current or counter-current chilled cooling gas.

Figure 3:
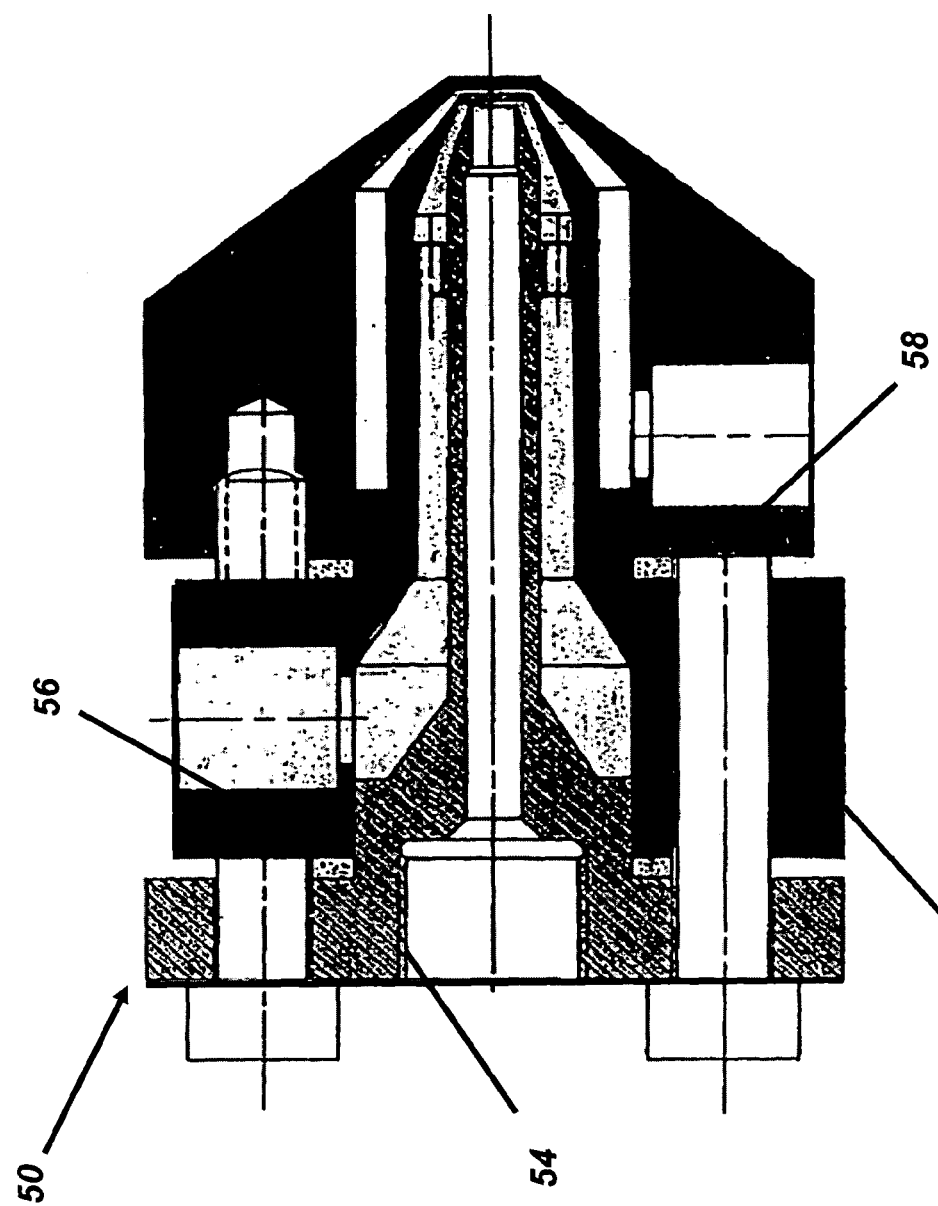
FIG. 3 is a cross-sectional view of a three fluid nozzle for use in the method of the present invention.
Figure 4A:
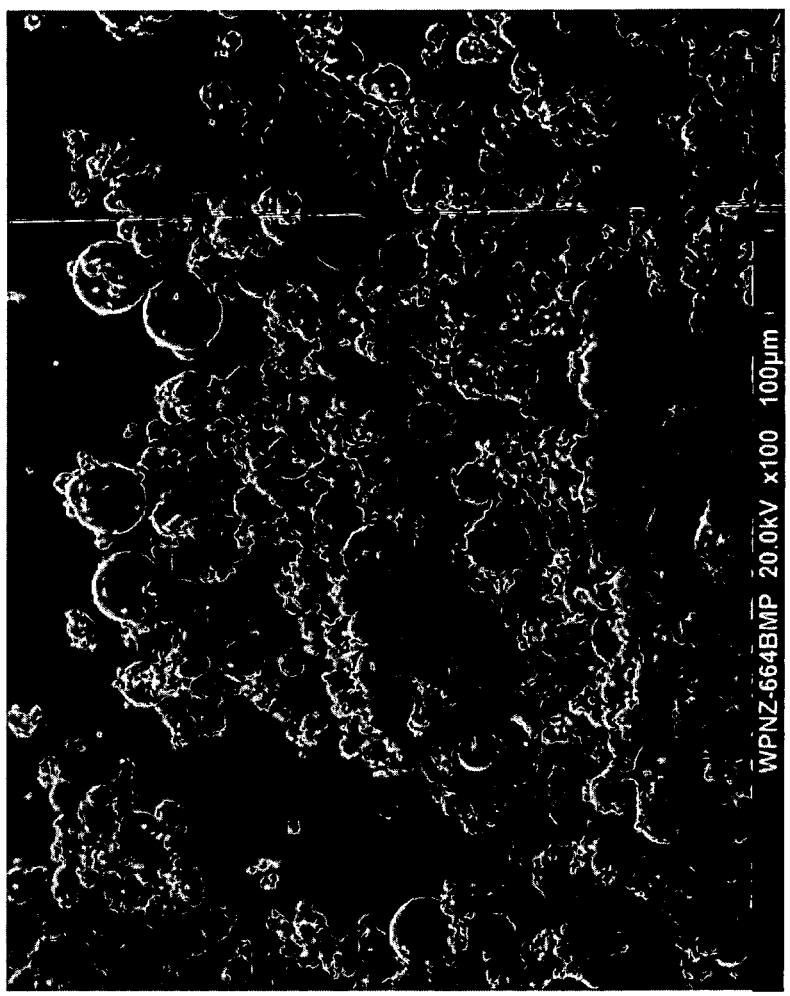
FIG. 4A is a scanning photomicrograph of a micro-prilled poloxamer prepared according to the present invention at a magnification of 100×.
Figure 4B:
FIG. 4B is a scanning photomicrograph of a micro-prilled poloxamer prepared according to the present invention at a magnification of 500×.

A cross-sectional view of a three fluid atomizing nozzle is shown generally at 50 in FIG. 3. The nozzle 50 includes a nozzle body 52 having three passages there thru. A first passage 54 is centrally located. A second passage 56 is located concentrically to the first passage 54. Finally, a third passage 58 is concentric to both the first and the second passages, 54, 56. All three passages 54, 56, and 58 have a common exit at the end of the nozzle 50. In use an atomizing gas is passed through the first and third passages 54, 58 and the fluid to be atomized is passed through the second passage 56. The fluid is sheared between the two gas streams and generally the third passage 58 has lower gas velocity relative to the first passage 54 because of its larger sized opening. A plurality of nozzles 50 can be mounted in the top of a standard prilling tower and feed atomized droplets into the co-current or counter-current chilled cooling gas.

As discussed above in the standard method of forming large sized prills using nozzles 20, 20', or 50 the standard operating conditions are pressures of from about 50 to 70 psig and liquid feed temperatures of 93 to 99° C. The atomizing gas is generally held at 25° C. or at least is not heated. The prills produced have a general size range of 400 to 1200 microns. Surprisingly, the present inventors have found a method for creating spherical particles or poloxamer with an average size of less than or equal to 106 microns by drastically changing the usual operating parameters of an atomizing process and use of the prilling tower.

More specifically, it has been found that increasing the atomizing pressure is very beneficial to production of appropriate droplets. Preferably the atomizing pressure using either the two fluid or three fluid nozzle is increased to from 100 to 150 psig and more preferably to from 115 to 150 psig. This is an increase of over two-fold above previous pressures. In addition, a reduction of the viscosity of the poloxamer is very beneficial. Preferably the viscosity is reduced to less than or equal to 1300 cps, more preferably to less than or equal to 750 cps, and most preferably to less than or equal to 300 cps. This reduction in viscosity is best accomplished by heating the poloxamer to much higher temperatures than previously used. As would be understood by one of ordinary skill in the art the effect of temperature on viscosity is dependent to a large extent on the structure of the poloxamer. In Table 1 below the effect of temperature on viscosity of two poloxamers, BASF Corporation Poloxamer 188 and 407, useful in the present invention is shown.

TABLE 1

| Temperature, ° Celsius | Poloxamer 188, viscosity in cps | Poloxamer 407, viscosity in cps |
| --- | --- | --- |
| 93.3 | 536 | 1411 |
| 104.4 | 419 | 978 |
| 115.5 | 334 | 700 |
| 126.6 | 272 | 514 |
| 137.8 | 224 | 387 |
| 148.9 | 187 | 297 |
| 160.0 | 158 | 231 |
| 171.1 | 135 | 183 |
| 182.2 | 117 | 147 |
| 193.3 | 101 | 120 |

As can be seen from Table 1, for the noted poloxamers temperatures over about 105° C. rapidly decrease the viscosity and the present inventors have found that temperatures of greater than this dramatically improve particle formation. Most poloxamers of interest in the present invention have char points of about 210° C., thus it is beneficial to keep the poloxamer below these temperatures. Preferred temperatures for the poloxamers useful in the present invention range from about 120 to 205° C., and more preferably from about 125 to 195° C. This can be accomplished by using heated storage tanks for the poloxamers and heated lines for delivery of the poloxamer to the atomizing nozzle. Alternatively, the poloxamer can be heated by passing it through a heat exchanger as it is fed to the atomizing nozzle. These temperatures are well above the previously used temperatures and produce the unexpected benefit of much better droplet formation in the desired size range.

Additional improvements in droplet formation have been found by heating the atomizing gas. Preferably the atomizing gas is heated to a temperature of from about 80 to 140° C. Initially when the liquid stream is broken up the particles are not round but typically in ribbons or threads. Given enough time the atomized material takes a spherical form. If the atomizing gas is at ambient temperature or cool the stream may freeze too quickly in the prilling tower, resulting in the atomized material freezing before it has a chance to take on a spherical shape. The resulting non-spherical material will have a reduced flowability, which is a disadvantage when handling and mixing the material. Adjusting the atomizing gas temperature to a higher temperature has been found to delay the freezing until the atomized droplets obtain a spherical shape. It has also been found that the flow rate of liquid to gas pressure has a significant affect on droplet formation. Specifically, reducing the liquid flow increases formation of droplets in the desired size range. Preferably, the liquid flow rate is less than or equal to 60 kilograms per hour, more preferably less than 45 kilograms per hour and most preferably less than 30 kilograms per hour. After reviewing the present disclosure, those skilled in the art will recognize that the dimensions of the nozzle affect the atomization performance with smaller nozzles favoring smaller droplet sizes. In particular, liquid droplets obtained at a particular flow rate in a given nozzle can be decreased in size by increasing the gas pressure. There is however a limiting value that the gas pressure can be increased. Beyond the limiting value the gas flow becomes choked and further increases in pressure will not result in a decrease in droplet size. The exact value of the choking pressure is dependent on the nozzle geometry. From the present specification one skilled in the art will be able to vary the poloxamer feed temperature, atomizing gas pressure and poloxamer feed rate for any nozzle to produce nearly all the particles within the desired particle size range. The discussion above has taught that the best conditions for formation of droplets in the desired size range are generally the highest poloxamer feed temperature that can be tolerated without degradation of the poloxamer, a higher than normal gas pressure up to choking pressure, and as low a poloxamer feed rate as economically feasible. In practice, a temperature somewhat less than maximal is often chosen, as too small a particle size distribution could affect flowability of the particles and unnecessary energy input beyond what is necessary to make an acceptable product size distribution raises the utility costs.

Typically, the product collected from the prilling tower is further sieved to remove any oversized particles. Such sieving is optional depending on the atomizing conditions chosen. As noted with the proper atomizing conditions sieving may not be necessary. Even under optimal conditions; however, it has been found that sieving out of oversized particles may be necessary. These occur because of fluctuations in the operating parameters and due to agglomeration of the product in the prilling tower. Droplets that do not totally solidify in sufficient time can be blown by the cooling gas or atomizing gas currents into other droplets or solid particles and form agglomerations. These non-solid forms may also accumulate within the tower on tower structures. These deposits can grow during the prilling process and occasionally fall into the collected product. These potential problems can be greater in a counter-current prilling tower because the cooling gas is blowing the particles upward and back toward the nozzle or nozzles. In a co-current prilling tower the cooling gas is flowing downward away from the nozzle or nozzles so this is less of a problem. In summary, one of skill in the art will readily determine if sieving is desired depending on the operating parameters. Such sieving can be accomplished with standard sieving equipment such as a Centri-Sifter from Kason, Inc. To measure the actual particle size distribution a Micron Air Jet Sieve® available from Hosokawa Micron International, Inc. is used. For the present invention the product obtained from the prilling tower preferably is sieved through a 140 mesh screen, having openings of approximately 106 microns, and collected. It is preferable that the product obtained has a size distribution such that about 50% or more passes through a 270 mesh screen, having openings of about 53 microns.

EXAMPLE 1

Poloxamer 188 was atomized in an internal mixing two fluid nozzle from Spray Systems, Inc. number 1/4J-SS-PF50264-80100DF+245-SS and sprayed into a counter-current prilling tower. The atomization conditions were as noted in Table 2 below. The atomizing gas, nitrogen, was maintained at 96° C. The product collected from the prilling tower was then sieved though 140 and 270 mesh screens to determine the percentage retained on the 140 mesh screen and the percentage on the 270 mesh screen. Representative results are shown in Table 2. Notice the sample prepared at a poloxamer temperature of 149.6° C. yielded a product wherein the nominal average particle size was less than the 53 microns of the mesh. Preferably for the present invention the plurality of particles obtained have an average nominal diameter of less than or equal to 106 microns. For certain atomizing conditions this may require sieving of the obtained product.

TABLE 2

| Poloxamer temp., ° C. | Atomizing pressure, psig | Poloxamer flow rate kg/hr | % retained on 140 mesh | % retained on 270 mesh |
| --- | --- | --- | --- | --- |
| 132.5 | 120 | 32 | 25 | 56 |
| 128.7 | 150 | 50 | 41 | 75 |
| 135.8 | 120 | 31.5 | 16 | 53 |
| 118.8 | 120 | 60 | 38 | 66 |
| 149.6 | 120 | 28 | 6 | 35 |
| 136.4 | 120 | 28 | 12 | 45 |
| 121.5 | 120 | 40 | 32 | 66 |
| 138.6 | 120 | 42 | 26 | 60 |
| 160.6 | 150 | 46 | 30 | 66 |

EXAMPLE 2

Poloxamer 407 was atomized in the internal mixing two fluid nozzle from Example 1 and sprayed into a counter-current prilling tower. The atomization conditions were as noted in Table 3 below. The atomizing gas, nitrogen, was maintained at 88° C. The product collected from the prilling tower was then sieved though 140 and 270 mesh screens to determine the percentage retained on the 140 mesh screen and the percentage on the 270 mesh screen. Representative results are shown in Table 3. Note that the poloxamer run at a temperature of 157.3° C. had a particle size distribution such that over 50% were less than 53 microns.

TABLE 3

| Poloxamer temp., ° C. | Atomizing pressure, psig | Poloxamer flow rate kg/hr | % retained on 140 mesh | % retained on 270 mesh |
| --- | --- | --- | --- | --- |
| 158.4 | 120 | 23.5 | 13 | 46 |
| 138.6 | 120 | 55 | 48 | 78 |
| 136.4 | 120 | 21 | 15 | 49 |
| 135.3 | 150 | 50 | 49 | 80 |
| 153.4 | 120 | 26 | 13 | 43 |
| 157.3 | 120 | 25 | 9 | 42 |

To compare the poloxamer prepared according to the present invention to the micro-milled poloxamer in a pharmaceutical preparation a three fluid nozzle, Nubilosa model 10 B 16 V was used to atomize Poloxamer 407. The micro-milling of Poloxamer 407 was carried out as described above. The poloxamer was atomized at a feed temperature of 150° C., pressure of 80 psig in a counter-current prilling tower. The product was sieved through a 140 mesh screen. The product passing through the 140 mesh screen was collected. This product had a size distribution of 69.4% passing through a 270 mesh screen and 30.6% collected on it. The micro-milled (MM) and the micro-prilled (MP) products were evaluated at two levels, high and low, using three different tablet formation processes. The medicament used was carbamazepine. The formulations were processed by direct compression (DC), wet granulation (WG), or melt granulation (MG) at two levels of the MM or MP poloxamer. The formulas are given below in Table 4. Ludipress® is a tableting aid from BASF Corporation that is a combination of lactose, povidone, and crospovidone. The following abbreviations are used in the table: C is carbamazepine; MM is micro-milled Poloxamer 407; MP is micro-prilled Poloxamer 407; L is Ludipress®; LM is lactose monohydrate; HPMC is hydroxypropylmethyl cellulose; CS is croscarmellos sodium; MS is magnesium stearate.

TABLE 4

| Formulation | C, gm | MM, gm | MP, gm | L, gm | LM | HPMC | CS | MS |
| --- | --- | --- | --- | --- | --- | --- | --- | --- |
| DC | 40.0 | 10.0 | | 49.5 | | | | 0.5 |
| DC | 40.0 | | 10.0 | 49.5 | | | | 0.5 |
| DC | 40.0 | 20.0 | | 39.5 | | | | 0.5 |
| DC | 40.0 | | 20.0 | 39.5 | | | | 0.5 |
| WG | 40.0 | 10.0 | | | 43.5 | 3.0 | 3.0 | 0.5 |
| WG | 40.0 | | 10.0 | | 43.5 | 3.0 | 3.0 | 0.5 |
| WG | 40.0 | 20.0 | | | 33.5 | 3.0 | 3.0 | 0.5 |
| WG | 40.0 | | 20.0 | | 33.5 | 3.0 | 3.0 | 0.5 |
| MG | 40.0 | 10.0 | | | | | 3.0 | 0.5 |
| MG | 40.0 | | 10.0 | | | | 3.0 | 0.5 |
| MG | 40.0 | 20.0 | | | | | 3.0 | 0.5 |
| MG | 40.0 | | 20.0 | | | | 3.0 | 0.5 |

For the direct compression the carbamazepine, poloxamer, and ludipress® were blended for 15 minutes, then the magnesium stearate was added and the blending continued for another minute. For the wet granulation the carbamazepine, poloxamer, LM, and HPMC were blended for 5 minutes. Then a granulation was prepared using water as the granulation media. The granulation was dried overnight on a tray in an oven at 45° C. Then the CS was added to the dried granulation and blended for 2 minutes. Finally, the MS was added and the granulation was blended for another minute. For the melt granulation the carbamazepine, poloxamer, and LM were blended for 5 minutes. The blend was placed in a water bath at 70° C. to melt the poloxamer. The resulting granule was rapidly cooled in an ice water bath. Then the CS was added and blended for 2 minutes. Finally, the MS was added and blended for a minute.

The blend homogeneity was tested for all the formulations by filling capsules for each formulation with 500 mg of each blend. Dissolution testing was carried out for one hour using water as the dissolution media with analysis of the carbamazepine by UV spectrophotometry at 284 nm. The results showed that there were no significant differences between any of the formulations or methods of preparation of poloxamer. Because the carbamazepine is a poorly soluble drug dissolution testing was also carried out in a mixture of water and ethanol (70:30) to enhance its dissolution. All of the formulations showed the same drug release pattern with no significant differences and all showed complete release at 2 hours.

Each formulation was then compressed into tablets using a 7/16 inch round standard concave tooling on a Korsch XL-100 press at 25 rpm. The target weight for the tablets was 500 mg and they were compressed using compressive forces of 10, 15, or 20 KNewtons. The formed tablets were tested in process for weight, hardness, disintegration and friability. There were no significant differences in the formulations of these measures. The friability ranged from 0.1% to 0.5%.

The results demonstrate that there are or no physical differences in formulations prepared using the micro-milled or micro-prilled poloxamer. Preferably, the micro-prilled poloxamer particles are used in an amount of from about 10 to 50% by weight based on the total formulation weight of a pharmaceutical. The micro-prilled poloxamer particles are useful in all classes of medicament, but especially useful in formulations of poorly soluble or low permeability medicaments of class II defined as low solubility and high permeability or in class IV defined as low solubility and low permeability. Non-limiting examples of class II drugs include: carbamazepine, methadone, propranolol, metoprolol, carvedilol, timolol, atenol, meperidine, cocaine, amphetamine, phenmetrazine, and methylphenidate. Non-limiting examples of class IV drugs include: diltiazem, amlodipine, verapamil, benzodiazepine, and chloral hydrate. There are, however, significant differences in the cost-effectiveness and ease of preparation. The micro-prilled process disclosed in the present invention is a significant step forward in creating poloxamer particles that find special use in pharmaceuticals. The process is much more rapid, can be done in a system with much less exposure to the environment and fewer handling steps, and does not require highly specialized equipment.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

We claim:

1. A method for formation of a plurality of micro-prilled poloxamer particles comprising the steps of:
    a) providing at least one copolymer of ethylene oxide and propylene oxide having a general formula of $HO(C_2H_4O)_a(C_3H_6O)_b(C_2H_4O)_aH$, wherein a value of a is from about 60 to about 150 and a value of b is from about 25 to about 60;
    b) heating the at least one copolymer of step a) to a temperature sufficient to reduce its viscosity to less than or equal to 1300 cps, provided that the temperature is less than a char temperature of the at least one copolymer of step a);
    c) atomizing the heated at least one copolymer from step b) by passing it through an atomizing nozzle and into one of a co-current or a counter-current prilling tower thereby forming a plurality of particles of said at least one copolymer, said plurality of particles having an average nominal diameter of less than or equal to 106 microns, wherein said plurality of particles are free of a medicament; and optionally
    d) sieving said plurality of particles formed in step c) and retaining the particles passing through a mesh screen having openings of about 106 microns.

2. The method as recited in claim 1, wherein step a) comprises providing at least one copolymer of ethylene oxide and propylene oxide having a number average molecular weight of from about 6000 to about 18000 Daltons.

3. The method as recited in claim 1, wherein step a) comprises providing at least one copolymer selected from the group consisting of $HO(C_2H_4O)_a(C_3H_6O)_b(C_2H_4O)_aH$ with a having a value of about 80 and with b having a value of about 27; $HO(C_2H_4O)_a(C_3H_6O)_b(C_2H_4O)_aH$ with a having a value of about 64 and with b having a value of about 37; $HO(C_2H_4O)_a(C_3H_6O)_b(C_2H_4O)_aH$ with a having a value of about 141 and with b having a value of about 44; $HO(C_2H_4O)_a(C_3H_6O)_b(C_2H_4O)_aH$ with a having a value of about 101 and with b having a value of about 56; and mixtures thereof.

4. The method as recited in claim 1, wherein step b) comprises heating the at least one copolymer to a temperature of from about 120° C. to about 205° C.

5. The method as recited in claim 1, wherein step b) comprises heating the at least one copolymer to a temperature of from about 125° C. to about 195° C.

6. The method as recited in claim 1, wherein step c) comprises passing the copolymer of step b) through one of a two fluid atomizing nozzle or a three fluid atomizing nozzle.

7. The method as recited in claim 6 wherein the nozzle is selected to be a two fluid atomizing nozzle and a pressure of an outer gas is set at from about 100 to about 150 psig.

8. The method as recited in a claim 7, further comprising setting the outer gas at a temperature of from about 80 to about 140° C.

9. The method as recited in claim 7, wherein the outer gas is selected from the group consisting of nitrogen, air, oxygen, helium, and argon.

10. The method as recited in claim 6 wherein the nozzle is selected to be a three fluid atomizing nozzle and a pressure of an inner gas is set at from about 100 to about 150 psig and a pressure of an outer gas is set at from about 100 to about 150 psig.

11. The method as recited in a claim 10, further comprising setting both the inner and the outer gas at a temperature of from about 80 to about 140° C.

12. The method as recited in claim 10, wherein both the inner and the outer gas are selected from the group consisting of nitrogen, air, oxygen, helium, and argon.

13. A method for formation of a pharmaceutical preparation comprising the steps of:
    a) providing at least one copolymer of ethylene oxide and propylene oxide having a general formula of $HO(C_2H_4O)_a(C_3H_6O)_b(C_2H_4O)_aH$, wherein a value of a is from about 60 to about 150 and a value of b is from about 25 to about 60;
    b) heating the at least one copolymer of step a) to a temperature sufficient to reduce its viscosity to less than or equal to 1300 cps, provided that the temperature is less than a char temperature of the at least one copolymer of step a);
    c) atomizing the heated at least one copolymer from step b) by passing it through an atomizing nozzle and into one of a co-current or a counter-current prilling tower thereby forming a plurality of particles of said at least one copolymer, said plurality of particles having an average nominal diameter of less than or equal to 106 microns, wherein said plurality of particles are free of a medicament; optionally
    d) sieving said plurality of particles formed in step c) and retaining the particles passing through a mesh screen having openings of about 106 microns; and
    mixing the particles retained in step d) or c) with a medicament.

14. The method as recited in claim 13, comprising mixing the particles in an amount of from 10 to 50% by weight based on the total weight of the pharmaceutical preparation.

15. The method as recited in claim 13, comprising selecting the medicament from the group consisting of carbamazepine, methadone, propranolol, metoprolol, carvedilol, timolol, atenol, meperidine, cocaine, amphetamine, phenmetrazine, methylphenidate, diltiazem, amlodipine, verapamil, benzodiazepine, and chloral hydrate.

16. A plurality of micro-prilled poloxamer particles formed in accordance with the method set forth in claim 1, said particles comprising:
one or more copolymers of ethylene oxide and propylene oxide each having a general formula of $HO(C_2H_4O)_a(C_3H_6O)_b(C_2H_4O)_aH$, wherein a value of a is from about 60 to about 150 and a value of b is from about 25 to about 60;
said particles being spherical, solid at 25° C., and said plurality of particles having an average nominal diameter of less than or equal to 106 microns;
wherein said plurality of particles are free of a medicament.

17. The plurality of micro-prilled poloxamer particles as recited in claim 16, wherein said one or more copolymers each have a number average molecular weight of from about 6000 to about 18000 Daltons.

18. The plurality of micro-prilled poloxamer particles as recited in claim 16, wherein said one or more copolymers are selected from the group consisting of $HO(C_2H_4O)_a(C_3H_6O)_b(C_2H_4O)_aH$ with a having a value of about 80 and with b having a value of about 27; $HO(C_2H_4O)_a(C_3H_6O)_b(C_2H_4O)_aH$ with a having a value of about 64 and with b having a value of about 37; $HO(C_2H_4O)_a(C_3H_6O)_b(C_2H_4O)_aH$ with a having a value of about 141 and with b having a value of about 44; $HO(C_2H_4O)_a(C_3H_6O)_b(C_2H_4O)_aH$ with a having a value of about 101 and with b having a value of about 56; and mixtures thereof.

19. A pharmaceutical preparation comprising the plurality of micro-prilled poloxamer particles as recited in claim 16 and a medicament.

20. The pharmaceutical preparation as recited in claim 19, wherein said plurality of micro-prilled poloxamer particles are present in an amount of from about 10 to about 50% by weight based on the total weight of said pharmaceutical preparation.

21. The pharmaceutical preparation as recited in claim 19, wherein said medicament is selected from the group consisting of carbamazepine, methadone, propranolol, metoprolol, carvedilol, timolol, atenol, meperidine, cocaine, amphetamine, phenmetrazine, methylphenidate, diltiazem, amlodipine, verapamil, benzodiazepine, and chloral hydrate.

* * * * *